(12) United States Patent
Bailey, III et al.

(10) Patent No.: US 7,164,282 B1
(45) Date of Patent: Jan. 16, 2007

(54) METHODS AND APPARATUS FOR DETERMINING AN AVERAGE ELECTRICAL RESPONSE TO A CONDUCTIVE LAYER ON A SUBSTRATE

(75) Inventors: Andrew D. Bailey, III, Pleasanton, CA (US); Michael Leonard, Hayward, CA (US); Benjamin W. Mooring, Austin, TX (US); Candi Kristoffersen, San Jose, CA (US)

(73) Assignee: Lam Research Corporation, Fremont, CA (US)

( * ) Notice: Subject to any disclaimer, the term of this patent is extended or adjusted under 35 U.S.C. 154(b) by 100 days.

(21) Appl. No.: 11/092,849

(22) Filed: Mar. 28, 2005

(51) Int. Cl.
*G01R 31/26* (2006.01)
(52) U.S. Cl. .................................................. 324/765
(58) Field of Classification Search ............... None
See application file for complete search history.

(56) References Cited

U.S. PATENT DOCUMENTS

| | | | |
|---|---|---|---|
| 4,849,694 A | 7/1989 | Coates | |
| 6,333,638 B1 * | 12/2001 | Fukasawa et al. | 324/765 |
| 7,002,363 B1 * | 2/2006 | Mathieu | 324/758 |

OTHER PUBLICATIONS

Dusharme, "New Trends in Eddy Current Testing," http://www.qualitydigest.com/dec05/articles/01_article.shtml, 7 pp, Dec. 2005.

Welsby et al., "True Position Measurement with Eddy Current Technology," Nov. 1997, http://www.sensormag.com/articles/1197/eddy1197/main.shtml, 13 pp.

Baumgartner, "FEM Simulation of the Electromagnetic Field in Eddy Current Proximity Sensors," SENSOR 99; Seonsoren, Messaufnehmer & Systeme, 6 pp. May-2005.

Yang, Chen, "Inductive Eddy Current Sensors for Position/Displacement Measurement and Nano-Positioning," http://www.chenyang-ism.com/EddyCurrentDistance.htm, 3 pp. Jun. 2006.

* cited by examiner

*Primary Examiner*—Jermele Hollington
*Assistant Examiner*—Trung Q. Nguyen
(74) *Attorney, Agent, or Firm*—IP Strategy Group, P.C.

(57) ABSTRACT

A method of determining an average electrical response to a conductive layer on a set of substrates vibrating about a vibration mean is disclosed. The method includes positioning a sensor near a position on a first substrate; and measuring a first plurality of electrical responses, wherein each of the first plurality of electrical responses is function of an electrical film property response and a first substrate proximity response. The method also includes positioning the sensor near the position on a second substrate; and measuring a second plurality of electrical responses, wherein each of the second plurality of electrical responses is function of the electrical film property response and a second substrate proximity response. The method further includes determining a first average electrical response for the first substrate and a second average electrical response for the second substrate, wherein a difference between an average first substrate proximity response and an average second substrate proximity response is about zero.

20 Claims, 6 Drawing Sheets

METHODS AND APPARATUS FOR DETERMINING AN AVERAGE ELECTRICAL RESPONSE TO A CONDUCTIVE LAYER ON A SUBSTRATE

BACKGROUND OF THE INVENTION

The present invention relates in general to substrate manufacturing technologies and in particular to methods and apparatus for determining an average electrical response to a conductive layer on a substrate.

In the processing of a substrate, e.g., a semiconductor wafer, MEMS device, or a glass panel such as one used in flat panel display manufacturing, plasma is often employed. As part of the processing of a substrate (chemical vapor deposition, plasma enhanced chemical vapor deposition, physical vapor deposition, etc.) for example, the substrate is divided into a plurality of dies, or rectangular areas, each of which will become an integrated circuit. The substrate is then processed in a series of steps in which materials are selectively removed (etching) and deposited (deposition) in order to form electrical components thereon.

Metals are particularly important materials in substrate manufacturing. For example, in a manufacturing method, known as dual damascene, dielectric layers are electrically connected by a conductive plug filling a via hole. Generally, an opening is formed in a dielectric layer, usually lined with a TaN or TiN barrier, and then subsequently filled with other conductive material (e.g., aluminum (Al), copper (Cu), tungsten (W), etc.) that allows electrical contact between two sets of conductive patterns. This establishes electrical contact between two active regions on the substrate, such as a source/drain region. Excess conductive material on the surface of the dielectric layer is typically removed by chemical mechanical polishing (CMP). A blanket layer of silicon nitride or silicon carbide may then be deposited to cap the copper.

Subsequently, in order to insure that the process is within acceptable parameters, it is often important to determine the electrical film properties (e.g., thickness, sheet resistance, etc.) of a conductive layer at a particular point on the substrate. One method of measurement is the use of eddy current sensors. Generally, eddy currents are currents that are induced in a conductive media by an alternating magnetic field.

In general, if a first alternating current is applied to a wire wrapped in a generally solenoidal shape (e.g., the wire in an eddy current sensor), a first alternating electromagnetic field forms in and around the solenoid extending beyond the ends of the solenoid a distance on the order of the diameter of the solenoid. If this first field is brought into proximity with a second conductor (e.g., a conductive layer on the substrate) a second alternating electrical current will also flow in the second conductor, causing a second field that interacts with (e.g., adds vectorally to) the first field and results in a perturbation to the field around the probe. These perturbations in the probe's initial field may cause detectable changes in the probe's electrical characteristics including the probe's impedance and frequency response. Using an impedance-voltage converter, the impedance change can be converted into a voltage change for further signal processing and analysis.

Many techniques are available for producing a signal from these detected differences in eddy current probe characteristics. For example, in a first technique, the width of the frequency dependent power absorption of the probe/eddy current sensor system (sensor system) can be reported. Likewise, in a second technique, the change in the magnitudes of the real and/or imaginary parts of the probe impedance can be reported between the probe and the second conductor. These measurements are generally made using passive or active circuitry to produce a range of voltages that can be bounded by the signal with no second conductor present and the signal with a second conductor causing maximal change in the signal. The exact shape, thickness and conductivity of the second conductor that causes the maximal change in the probe signal generally depends on the probe geometry, excitation frequency and the method adopted for measurement, but generally it is a thick (on the order of many times the diameter of the probe) conductive film placed as near to the probe as possible.

Depending on the application, conductive or magnetic elements can also be incorporated into the design of the probe in order to modify the spatial extent and magnitude of the probe field and hence the spatial and electrical sensitivity to the second conductive layer. For optimum performance, the sensor system should maximize sensor system sensitivity to the desired electrical property of the conductive film (e.g., thickness, sheet resistance, etc.) while minimizing the sensor system's sensitivity to all other effects and variables.

However, the electrical response of sensor to the magnetic field (eddy current perturbations), and hence its accuracy, may also be affected by the proximity (substrate proximity response) of the sensor to the substrate. That is, as the exciting probe field is of limited spatial extent and its magnitude decreases as the position increases from the probe, the overall eddy current perturbations caused by a second conductor being measured also decrease as the second conductor is moved further from the probe. Thus, an eddy current sensor may be sensitive to both proximity and electrical film properties. In general, it is difficult to isolate the portion of the electrical response caused by electrical film properties (electrical film property response) from the portion of the electrical response caused by proximity (substrate proximity response), which may subsequently introduce an error in the reported value.

Figure 1:
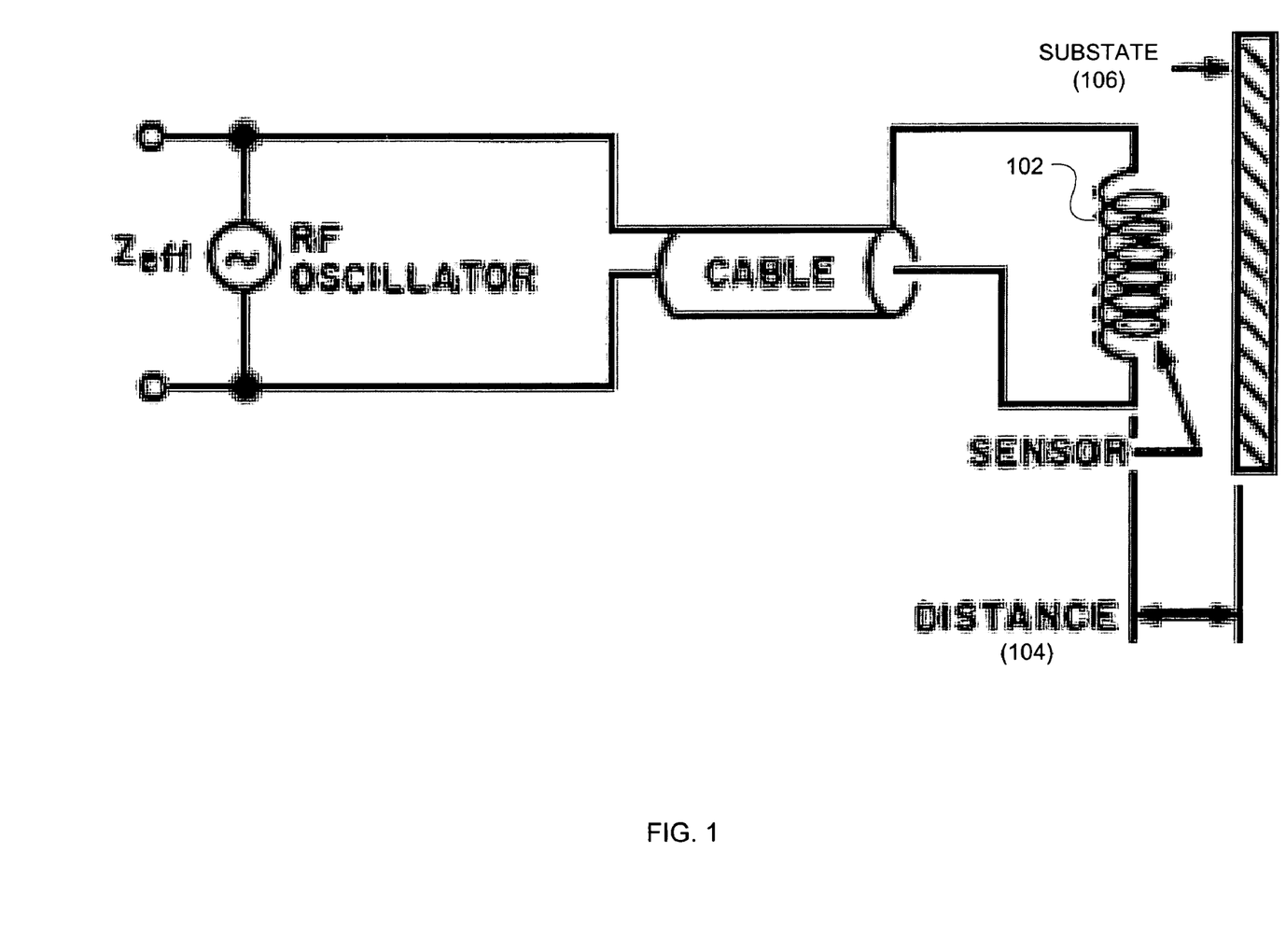
FIG. 1 illustrates a simplified diagram of an eddy current sensor.

Referring now to FIG. 1, a simplified diagram of an eddy current sensor is shown. Generally, changes in the sensor's coil impedance 102 are caused by varying the distance 104 between the sensor (coil) and substrate 106. Since the electrical parameters of target material resistivity and permeability may determine the magnitude of the measured sensor perturbation, the sensor system is generally calibrated for the target material.

One solution to improve the response of a given sensor may be to average out the proximity errors of multiple sensors, each concurrently trying to measure the same point on the substrate from the same proximity (e.g., concurrent multiple sensors). For example, two sensors, each with a known and fixed proximity to each other, may be positioned at a fixed proximity to a conductive layer positioned between them. In a common implementation, one sensor is positioned above the substrate and the other sensor is positioned below the substrate. If each sensor has a substantially identical sensitivity to proximity, the electrical response on any one sensor may be substantially equal but opposite to the electrical response on the other sensor. Subsequently, averaging together a signal from each sensor may result in a combined signal that is much less sensitive to the position (proximity) of the conductive layer to either one of the two sensors, and which subsequently may be used to better report the desired electrical property of the conductive film (e.g., more independent of proximity).

By periodically calibrating the sensor system (sensors, substrate geometry and substrate handling, stage movements, etc.) prior to making measurements, the proximity error in theory may be cancelled out by averaging a pair of measurements taken when the substrate is placed in the known position between the sensors. In practice, however, it is often very difficult to repeatably and precisely position the eddy current sensors with respect to the measured conductive layer.

For example, the equipment used to position a substrate between sensors may have a tolerance range that is too broad, so that the perturbations of the sensors due to changes in the substrate film thickness are substantially similar when compared to the sensor perturbations measured due the differing proximities at different measurement placements or times. Likewise, a mechanism used to move the substrate with respect to the sensors (i.e., turntable, etc.) may induce vibrations in the substrate or changes in the substrate proximity with amplitudes that cause perturbations in probe signals that exceed the measured differences in film thickness or introduce uncertainty in the reported film thickness in excess of the desired precision for the sensor system. Subsequently, even relatively small proximity variations may introduce substantial errors in the measurements, presenting a problem for high precision measurements, such as substrate manufacturing.

In addition, even if the proximity error for concurrent multiple sensors could be substantially minimized, it may still be desirable to make the measurements at different points in time (e.g., sequential measurement). For example, since sensors are often located on a sensor swing arm, it may be inconvenient to align both sensors when moving the sensor swing arm across the surface of the substrate. That is, two sensors may be placed on the sensor swing arm such that they form a line parallel to a vector that is tangent to the rotation of the substrate on a turntable. As the sensor arm swings across the rotating substrate, the angle between the sensor line and the tangent vector may increase to the point at which both sensors cannot be positioned over the same point on the substrate at the same time. Additionally, the sensor swing arm construction itself may prevent locating the sensors on top of each other, or interference from one sensor (e.g., cross talk) may prevent the simultaneous use of both sensors.

Figure 2:
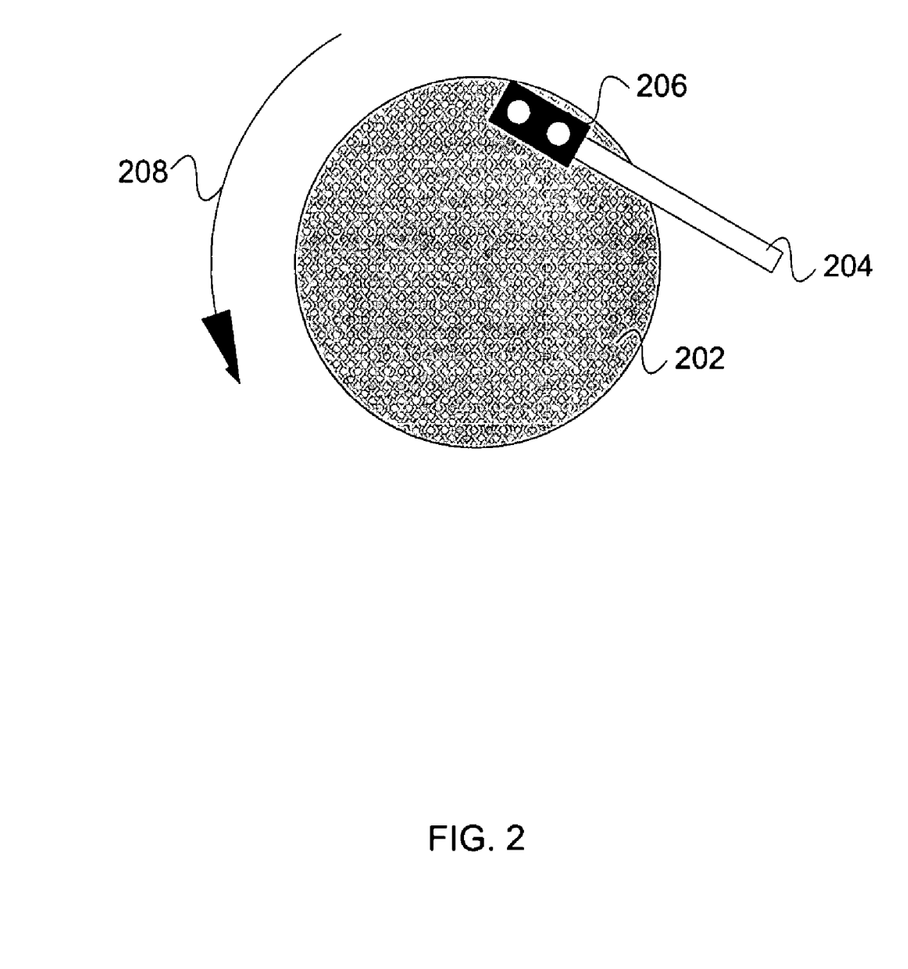
FIG. 2 illustrates a simplified diagram of a substrate on a turntable with a sensor arm.

Referring now to FIG. 2, a simplified diagram of a substrate in a mechanism to rotate it with a sensor arm is shown. In this example, substrate 202 rotates in direction 208, as sensor swing arm 204 moves sensors 206 across the surface of substrate 202.

In view of the foregoing, there are desired methods and apparatus for determining an average electrical response to a conductive layer on a substrate.

SUMMARY OF THE INVENTION

The invention relates, in one embodiment, to a method of determining an average electrical response to a conductive layer on a set of substrates vibrating about a vibration mean. The method includes positioning a sensor near a position on a first substrate; and measuring a first plurality of electrical responses, wherein each of the first plurality of electrical responses is function of an electrical film property response and a first substrate proximity response. The method also includes positioning the sensor near the position on a second substrate; and measuring a second plurality of electrical responses, wherein each of the second plurality of electrical responses is function of the electrical film property response and a second substrate proximity response. The method further includes determining a first average electrical response for the first substrate and a second average electrical response for the second substrate, wherein a difference between an average first substrate proximity response and an average second substrate proximity response is about zero.

The invention relates, in another embodiment, to a method of determining an average electrical response to a conductive layer on a substrate vibrating about a vibration mean. The method includes positioning a first sensor near a position on a first substrate; and measuring a first plurality of electrical responses, wherein each of the first plurality of electrical responses is function of an electrical film property response and a first substrate proximity response. The method also includes positioning a second sensor near the position on a the substrate; and measuring a second plurality of electrical responses, wherein each of the second plurality of electrical responses is function of the electrical film property response and a second substrate proximity response, and wherein a mean value of the first substrate proximity response and the second substrate proximity response is about zero. The method also includes determining an average response of the plurality of the first plurality of electrical responses and the second plurality of electrical responses.

The invention relates, in another embodiment, to an apparatus of determining an average electrical response to a conductive layer on a substrate vibrating about a vibration mean. The apparatus includes means of positioning a first sensor near a position on a first substrate; and means of measuring a first plurality of electrical responses, wherein each of the first plurality of electrical responses is function of an electrical film property response and a first substrate proximity response. The apparatus also includes means of positioning a second sensor near the position on a the substrate; and means of measuring a second plurality of electrical responses, wherein each of the second plurality of electrical responses is function of the electrical film property response and a second substrate proximity response, and wherein a mean value of the first substrate proximity response and the second substrate proximity response is about zero. The apparatus further includes means of determining an average response of the plurality of the first plurality of electrical responses and the second plurality of electrical responses.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

While not wishing to be bound by theory, it is believed by the inventor herein that positional variation can be advantageously used to substantially eliminate eddy current sensor proximity error, resulting in a more accurate electrical film property measurement for a conductive layer.

As previously described, the response of a sensor to eddy current perturbations is affected by proximity errors between the sensor and the measured conductive layer. Since the actual proximity of any given sensor during a placement of the sensor to measure a point tends to be difficult to determine, simply averaging the results at a given point of different measurements taken while positioned at the measurement point does not necessarily increase the overall accuracy of the sensor system's final reported result even if the accuracy of that given measurement is now better determined due to the averaging of some noise such as digitization errors, electronic noise, sensor warm up.

However, in a non-obvious way, if a mean proximity is first determined, then resulting signals may be combined to significantly correct for proximity errors and hence provide a more accurate reported result. That is, a reported result may be obtained with a mean proximity error of about zero from a sensor system without following the normal approach of attempting to force the sensor system to a constrained a priori proximity with placement error about zero. In one embodiment, the combined signal and mean proximity error of each sensor is recalculated for each new measurement position on the substrate. The mean proximities of subsequent substrates generally may be recalculated from scratch without degrading the reported results' near zero dependence on proximity.

Proximity errors can be caused by changes in proximity of the sensor with respect to a nominally static substrate or a change in the substrate position, (e.g., from loading at different times) with respect to the nominally static sensor supports. In general, sensor proximity errors are caused by mechanical factors (i.e., stepper motor vibrations, sensor swing arm vibrations, etc.) that can follow a normal, periodic or generally peaked distribution curve about a mean value. Generally, even in sensor systems without aggressive vibration mitigation designs (e.g., isolation tables, active isolation tables, finer resolution stepper motors, feedback controlled placement of sensors or substrates, hyper rigid assemblies etc.), the mean proximity of professionally designed sensor systems does not change in between repeated sensor placement at a measurement site or repeated loading and unloading of substrates to be measured. That is, sensor systems will tend to have a vibration mean.

Often the most difficult proximity variation to control is between movement of the substrate or the sensor. Once the sensor system is stabilized, there may still be proximity variations, but they are typically many times smaller than that caused by the larger motion of the wafer and probes themselves. Subsequently, by measuring a sufficient number of variations in the signals measured at a desired point on the substrate surface, the signal due to the desired electrical film property at that point can be determined with extremely high accuracy, independent of the magnitude of the proximity errors of a particular sensor system. That is, since the sensor to film mean proximity does not substantially change during the sensor system operation, the signals collected in this manner from at least two sensors may be combined to provide a signal with essentially zero sensitivity to any particular instance of measurement (e.g., the proximity sensitivity and error in the reported film thickness can be substantially eliminated). Thus any detected changes in the combined measured eddy current signals may be principally caused by changes in film properties (e.g., film thickness, sheet resistance, etc.).

Subsequently, it can be shown that by properly averaging the signals collected during variation of the proximity of at least two independent eddy current sensors (a first sensor I and a second sensor II), each with known spatial proximity to the other sensors and a conductive layer positioned between them, may be combined to make the proximity error in the reported film property substantially zero.

In general, each sensor response, R, can be modeled as a function of several key variables $$R(-)=R(d,p,S).  \quad\quad [\text{EQUATION 1}]$$

Where d is film thickness to be measured, p is proximity and S is generally the sensor serial number which is a short hand notation denoting the functional dependence of the response on all the information about the conversion of the detected perturbation of the particular eddy current probe's field by the measured film into a convenient measurement unit. In an embodiment, the convenient measurement unit is volts (V).

Figure 3:
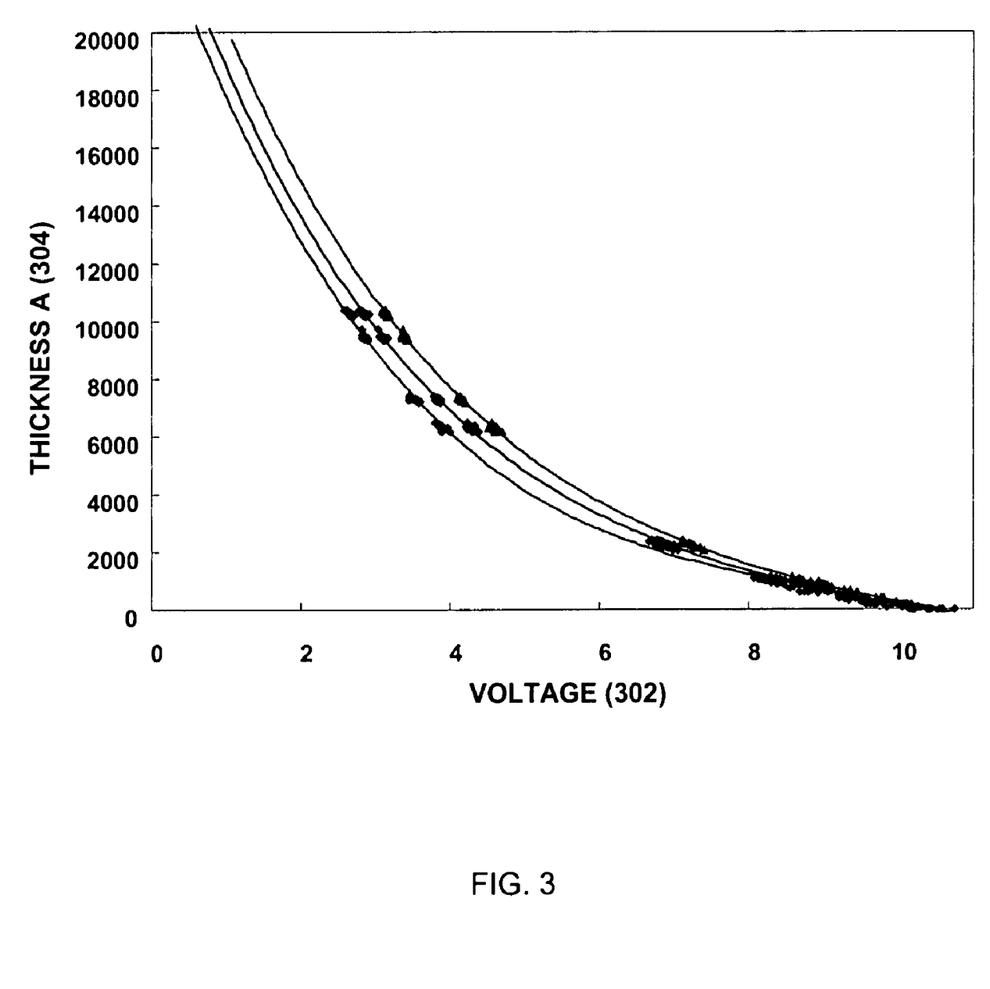
FIG. 3 illustrates a set of three calibration curves for determining the thickness of a conductive layer on a substrate, according to one embodiment of the invention.

Referring now to FIG. 3, a set of three calibration curves for determining the thickness of a conductive layer (i.e., Cu, etc.) on a substrate is shown, according to one embodiment of the invention. The vertical axis shows thickness 304 measured in Angstroms (A), while the horizontal axis shows the voltage response (V) 302 as measured by the eddy current sensor. In this example, a higher response voltage correlates to a smaller thickness. Calibration curves may also be created for the same purpose with the response voltage decreasing, e.g., by offsetting each probe response voltage by its maximum voltage obtained in the system with no film to be measured.

In a simplified example, the reported measurement V with reasonable proximity correction properties may be modeled as:

$$2V=R_I(d,p_I)+R_{II}(d,p_{II}) \approx R_I(d,p_I)+\epsilon_p \cdot dR_I/dp+R_{II}(d,p_{II})-\epsilon_p \cdot dR_{II}/dp \quad\quad [\text{EQUATION 2}]$$

where if $\epsilon_p$ is the proximity variation from p, at the actual time of the measurement for sensor I, then, inferring from the fixed geometry between sensor I and sensor II, $-\epsilon_p$ is the proximity variation from $p_{II}$ at the actual time of the measurement for sensor II if and only if the measurement from sensor II is made simultaneously. For purposes of this example, the sensor serial number S is assumed to be the same for all sensors, only d and p will be considered for purposes of the calculations. In addition, although the responses are shown in voltage, other electrical characteristics such as current may be used as well.

Both sensors are assumed have a substantially identical response at their nominal proximity $R(d,p_I)=R(d,p_{II})$ to film thickness. In practice, this can be reasonably done mechanically as mentioned below or with sensor dependent correlation functions. In addition, the response sensitivity for both sensors to proximity variation (e.g., proximity electrical response) is also assumed to be the same in magnitude but opposite in response. That is, one has a positive effect on the response and the other negative effect on the response. Subsequently, $dR_I/dp$ evaluated at $p_I$ equals $dR_{II}/dp$ evaluated at $p_{II}$.

In an embodiment, this may be accomplished by using a set of paired sensors of substantially the same type (hence about same performance) and loading the substrate halfway between them. Subsequently, the film may have the same nominal proximity to both sensors. Therefore, canceling out terms, the simplified reported measurement can be shown to be:

$$2V=2R(d)+0 \quad \text{[EQUATION 3]}$$

which may be independent of small proximity variations. In a simplified example, for a single sensor, if $R_I(d,p_I)=R_{II}(d,p_{II})=1.5V$, and if $dR_I/dp=2V/mm$, $\epsilon_p=0.1$ mm, then:

$$2V=R_I(d,p_I)+\epsilon_p \cdot dR_I/dp+R_{II}(d,p_{II})-\epsilon_p \cdot dR_{II}/dp=1.5V+ \\ 2V/nm*0.1\ mm+1.5V-2V/nm*0.1\ mm=3V \quad \text{[EQUATION 4]}$$

Thus in an ideal simultaneous measurement situation this method yields about 0% in proximity error or typically about $3\sigma<0.03V$. It should be clear that these analyses may be carried out with appropriate changes in weighting proportion between the two sensors in the sum in order to ensure cancellation of the relevant proximity terms or to include more than two sensors, but the fundamental properties described remain.

However, if the measurements are taken at different times, the corresponding proximity variations may also be different. That is, in reality the ideal situation is lost, since the proximity variation term $\epsilon_p$ is replaced with a more complex $\delta_p=\epsilon_p+s(t)$ where s(t) is a function of time.

Therefore, EQUATION 2 is now represented where nominal proximity notations are suppressed for clarity as $$2V=R_I(d,p_I)+R_{II}(d,p_{II})=R_I(d)+\delta_{pI} \cdot dR_I/dp+R_{II}(d_I)- \\ \delta_{pII} \cdot dR_{II}/dp \quad \text{[EQUATION 5]}$$

$$2V=R_I(d)+\epsilon_{p+}s(t_I) \cdot dR_I/dp+R_{II}(d_I)+ \\ (-\epsilon_p+s(t_{II})) \cdot dR_{II}/dp \quad \text{[EQUATION 6]}$$

$$2V=2R(d)+(s(t_I)+s(t_{II})) \cdot dR/dp \quad \text{[EQUATION 7]}$$

which may not be independent of small proximity variations except in very special cases where $s(t_I)+s(t_{II})=0$ for some reason. In addition, since this sum is not substantially constant among substrates, it generally can not be calibrated by subtracting a constant or other calibration. In general, common approaches aggressive vibration mitigation or hyper controlled sensor placement designs attempts to force this sum to zero. However, these approaches are generally costly to implement. In addition, uncompensated proximity variation errors in the reported measurement V still tend to remain in the calculation due to the remaining uncontrolled positional aspects of the sensor system.

The effect of uncompensated proximity for a single sensor may be substantial. For example, if $R_I(d)=R_{II}(d)=1.5V$, $dR/dp=2V/mm$, $s(t_I)=0.05$ mm, and $s(t_{II})=0.03$ mm, then $$2V=2R(d)+(s(t_I)+s(t_{II})) \cdot dR_I/dp=2*1.5V+2V/mm* \\ (0.05\ mm+0.03\ mm) \quad \text{[EQUATION 8]}$$

which yields >5% in proximity error, or about $3\sigma\sim0.15V$ or as much as three times the ideal case described in EQUATION 4 even though s(t) is a tenth of $\epsilon_p$.

Figure 4:
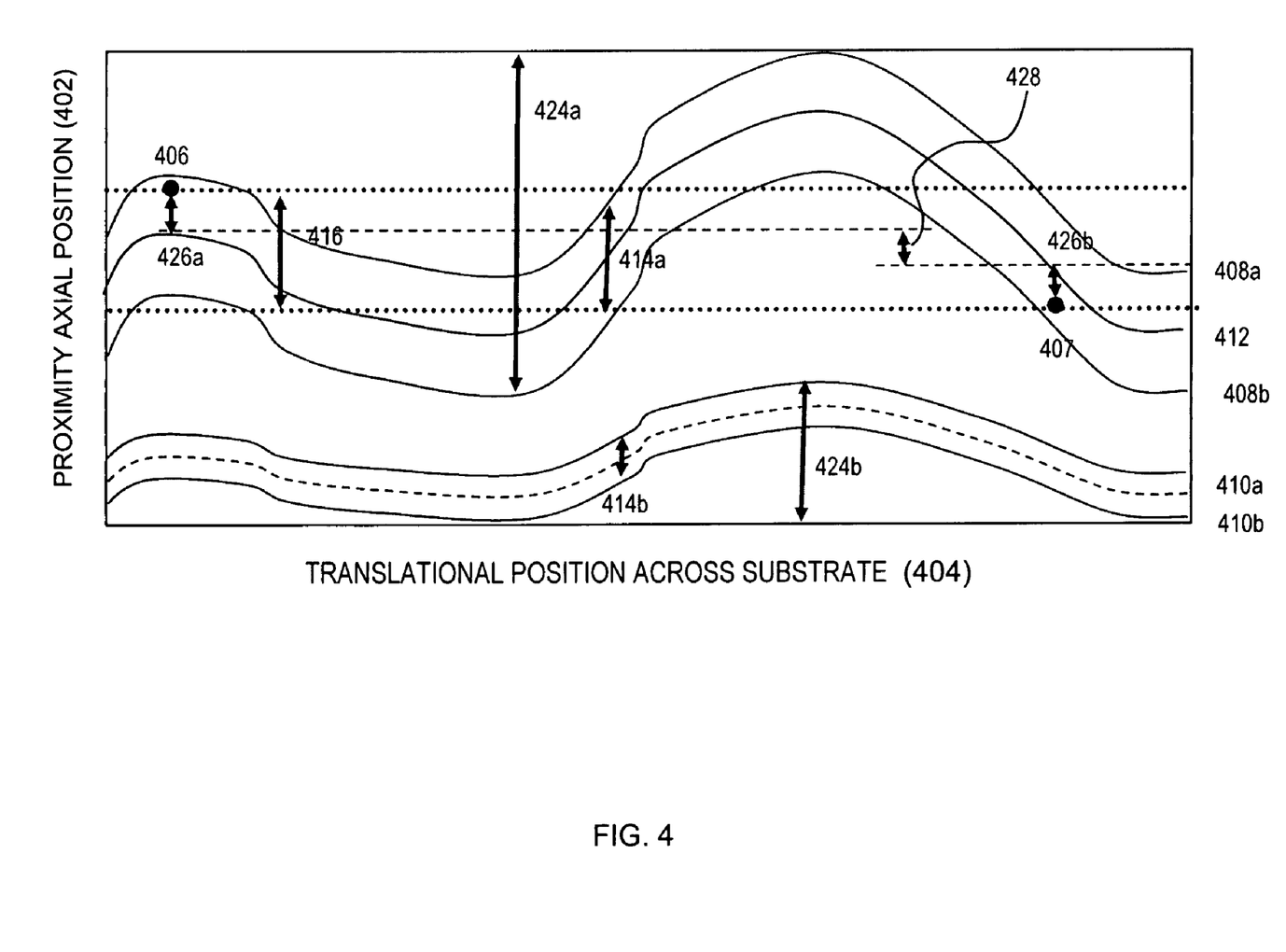
FIG. 4 illustrates a simplified diagram showing sensor proximity for a set of translational positions across the substrate.

Referring now to FIG. 4, a simplified diagram showing sensor proximity for a set of varied measurement instances of the substrate. For example, this diagram may represent the time evolution of vibrations in the sensor system, vibrations with time, or the variation in proximity between substrates, caused by substrate loading and unloading.

The vertical axis shows proximity axial position 402, while the horizontal axis shows varied measurement instance on substrate 404. In one configuration, the varied measurements may be at the same physical location, but at different times either because of motion of the sensor, the substrate or other mechanical elements in the sensor system. In another configuration, the varied measurements may be at different points on the wafer.

Lines 408*a–b* reflect the total variation in proximity to the substrate. Line 408*a* reflects the upper proximity variation range limit, whereas line 408*b* reflects the lower proximity variation range limit. The difference in ranges 414*a–b* reflect the portion of the proximity that may theoretically be reduced by isolating static sensor system vibrations (e.g., vibration settling for static measurements, isolation tables, active isolation tables, finer resolution stepper motors, feedback controlled placement of sensors or substrates, etc.). Likewise, the difference in ranges 424*a–b* reflect the portion of proximity variation that can be reduced by isolating dynamic sensor system vibrations (e.g., vibration settling for base lining loading a new wafer, finer resolution stepper motor calibration, feedback controlled placement of sensors or substrates, higher frequency sensor system calibration, etc.). Lines 410 reflect the variation in proximity that still remains after the sensor system vibrations have been isolated. Line 410*a* reflects the upper isolated range limit, whereas line 408*b* reflects the lower isolated range limit. Line 412 shows the mean of lines 408*a–b*.

Point 406 is a first proximity for a measurement at a first location and at a first measurement time, whereas point 407 is a second proximity for a measurement at a second varied position at either the first time but different location (e.g., concurrent multiple sensors), or at a second time (e.g., sequential measurement). As previously described, in either case, since the relative relationship between the proximities for the measurements are not known a priori and thus leaves unaccounted proximity errors in each signal there may exist a substantial variance 416 between the measurements thus leaving significant proximity errors in the sensor system's reported thickness even after combining the signals.

In addition, there may still exist a substantial variance 416 between the measurements at a first point at different times or from a second sensor. Even with the ideal case of combining these signals, there still remains an uncompensated difference between the proximity variations from the mean proximities 426*a–b*. That is, the portion of the electrical response caused by proximity variations may not cancel out.

In terms of the idealized model above the mean of the variance from the nominal proximity for point 406 is 426*a* ideally $\epsilon_p+s(t_I)$ and for point 407 is 426*b* ideally $\epsilon_p-s(t_{II})$. In the idealized case line 412 should be at the exact same proximity at both measurements 406 and 407 (i.e., assume the 426a minus 426b=s($t_I$)+s($t_{II}$)). Hence the variance 416 may be equivalent to the sum of the $p_I$ and $p_{II}$ while variance 416 minus the sum of variances 426a and 426b will be the uncompensated error s($t_I$)+s($t_{II}$). Note that these uncompensated uncertainties may be of the same type and remain even if the sensor system vibrations are isolated as shown by lines 410a–b.

In addition, although uncertainty may be partially reduced by averaging proximity variations after stopping the probe and substrate, and allowing vibration amplitudes to subside prior to making measurements, or by averaging multiple measurements from a sensor at a particular measurement instance, uncompensated proximity errors $c(e_{pI}-e_{pII})$ may still remain, as shown at 428.

For example, in a simplified model where c is the number of measurements taken at each site, which is assumed to be the same for both sensors, and the notation $e_{pI}$ and $e_{pII}$ denotes the non-varying proximity for each measurement instance in contrast to the idealized nominal proximities $\epsilon_{pI}$ and $\epsilon_{pII}$ respectively:

$$2V \cdot c = \Sigma R_I(d,p_I) + R_{II}(d,p_{II}) \approx cR_I(d) + \Sigma \delta_{pI} \cdot dR_I/dp + cR_{II}(d_I) - \Sigma \delta_{pII} \cdot dR_{II}/dp \quad \text{[EQUATION 8]}$$

$$2Vc = 2cR(d) + dR/dp \cdot \Sigma e_{pI} + s(t_I) + (-e_{pII} + s(t_{II})) \quad \text{[EQUATION 9]}$$

$$2Vc = 2cR(d) + c(e_{pI} - e_{pII}) \cdot dR/dp + \Sigma(s(t_I) + s(t_{II})) \cdot dR/dp \quad \text{[EQUATION 10]}$$

In general, as the sensor system settles, deviations s($t_I$) and s($t_{II}$) individually will tend to average or asymptotically approach zero. However, uncompensated proximity errors $c(e_{pI}-e_{pII})$, as shown at 428, may still remain, caused by the imprecise positioning of the sensor to the substrate between multiple substrates. In addition, the substrates themselves may have a concave or convex bow that introduces another proximity variable that leads to yet more deviations in the non-varying proximities of the particular measurement instances. Since, this error is not constant among substrates, it may not be accommodated by simple offset subtraction.

In a non-obvious way, the present invention may significantly improve proximity insensitivity to sensor system mechanical vibrations. In an embodiment, the proximity insensitivity is less than $1/10^{th}$. It is the inventors' belief that although mechanical sensor system vibrations may vary, the mean mechanical proximity between the sensors and substrate may be extremely stable from substrate to substrate, from substrate site to substrate site, and over long periods of time. Subsequently, a sensor system may be operating with the proximity vibrations of reasonably large magnitude and yet still produce sensor system reported values with near zero proximity error.

In an embodiment, a set of sensor signals are measured at designated substrate sites vibrating in a random or periodic motion with respect to the set of sensors. As previously described, for mechanical variations that have vibrations about a mean proximity for a site, averaging the signals may produce a mean signal for a given sensor that may quickly approach the true value of the signal combining the film thickness perturbation and the perturbation due to the mean proximity. That is, a mean mechanical proximity that is constant over time can be easily calibrated and removed from the reported sensor system value.

Figure 5:
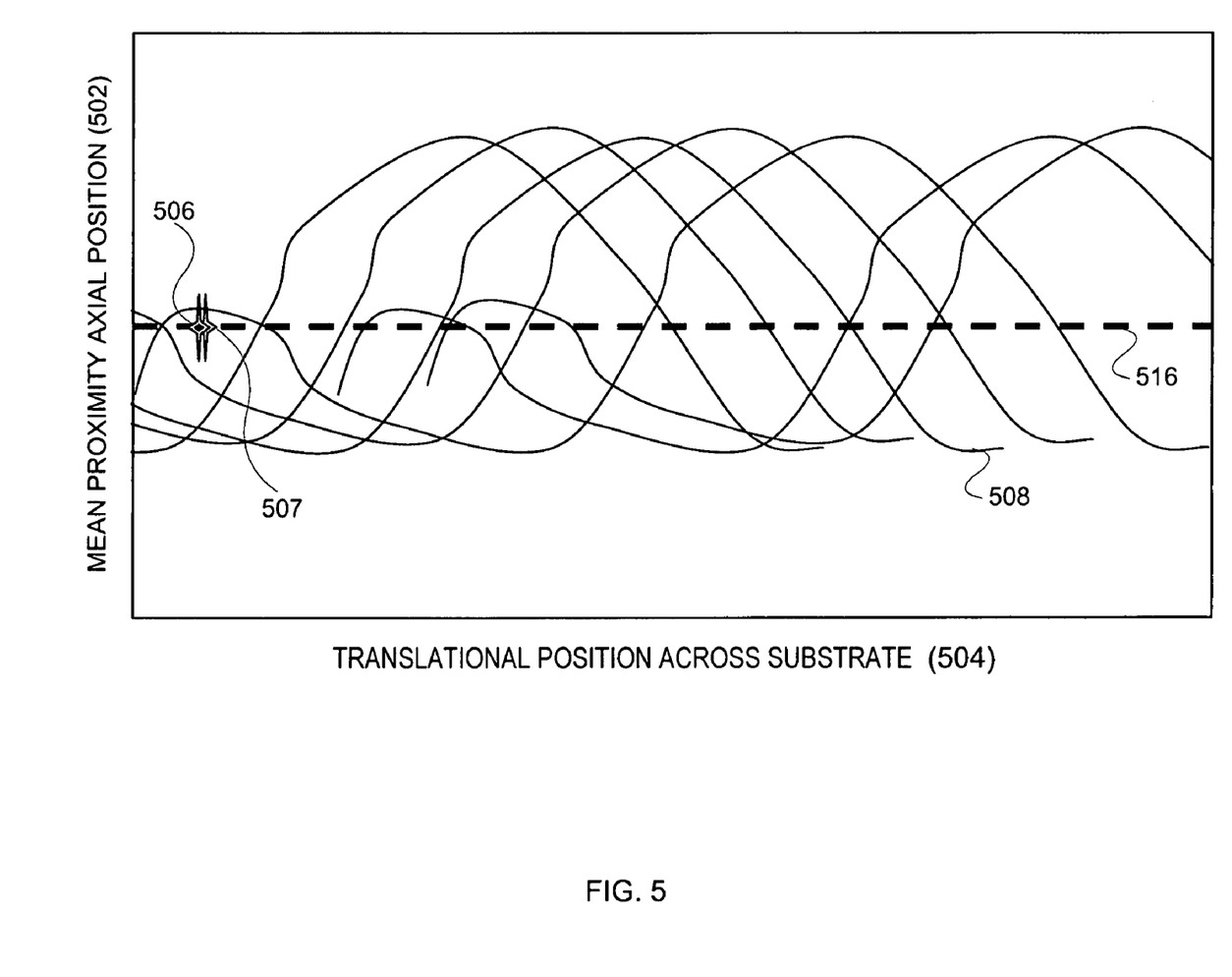
FIG. 5 shows a simplified diagram of mean sensor proximity for a set of translational positions across the substrate, according to one embodiment of the invention.

Referring now to FIG. 5, a simplified diagram of mean sensor proximity for a set of translational positions across the substrate is shown, according to one embodiment of the invention. The vertical axis shows proximity axial position 502, while the horizontal axis shows varied measurement instance on substrate 504. In one configuration, the varied measurements may be at the same physical location, but at different times either because of motion of the sensor, the substrate or other mechanical elements in the sensor system. In another configuration, the varied measurements may be at different points on the wafer.

Point 506 is a first proximity for a measurement at a first location and at a first measurement time, whereas point 507 is a second proximity for a measurement at a second varied position at either the first time but different location (e.g., concurrent multiple sensors), or at a second time (e.g., sequential measurement). Lines 508 reflect the total variation in proximity to the substrate. Line 506 represents mean proximity. Unlike as shown in FIG. 3, point 506 and point 507 are substantially the same value as mean proximity 516, which tends to be constant across measurements.

For example, in a simplified model where c is the number of measurements taken at each site, which is assumed to be the same for both sensors where the mean sensor to wafer proximities are now denoted with $P_I$ and $P_{II}$ to distinguish them from the idealized proximities $p_I$ and $p_{II}$ respectively:

$$R_I(d,P_I) = 1/c \Sigma R_I(d,p_I) \approx R_I(d,P_I) + 1/c \Sigma e_p \cdot dR_I/dp \quad \text{[EQUATION 11]}$$

Allowed proximity variations are schematically shown by repeating the proximity ranges 508 across all instances of measurement (i.e., substrate to substrate, substrate site to substrate site, measurement time to measurement time, etc.). Thus, the mean mechanical proximity 516 may be constant across measurements.

Since the mechanical errors are allowed to vary about their natural mean proximity, the average $1/c\Sigma e_p$ quickly approaches zero even with very large proximity variations due to either the near normal distribution of errors or the limited nature of e and the increasing denominator c. Subsequently, two combined signals are derived that may have the properties of the ideal measurement, and can thus utilize EQUATIONS 2 and 3 to result in a sensor system reported value that may be independent of small proximity variations to the mean mechanic positions without the restrictions in the idealized case that the sensors and substrate be positioned and measured simultaneously:

$$2V = R_I(d,P_I) + R_{II}(d,P_{II}) \approx R_I(d,P_I) + e_p \cdot dR_I/dp + R_{II}(d,P_{II}) - e_p \cdot dR_{II}/dp \quad \text{[EQUATION 12]}$$

Since this method ensures that each sensor's combined response may be independent of mechanical sensor system proximity variations, these responses can be calibrated to additional parameters of interest such as film thickness in units of Angstroms with high precision. The repeatability of the sensor system reported value is then very stable to proximity changes and any additional variations $e_p$ may be from unique and fixed proximity variations inherent in the measured substrate itself. Thus the same calibration will work wafer to wafer over very long periods of time.

In general, as long as sensor system vibrations remain substantially random for a given static sensor position, the mean proximity error of a set of independent eddy current sensors, each with a known time and space proximity to other sensors, and to a conductive layer positioned between them, may be substantially zero.

Figure 6:
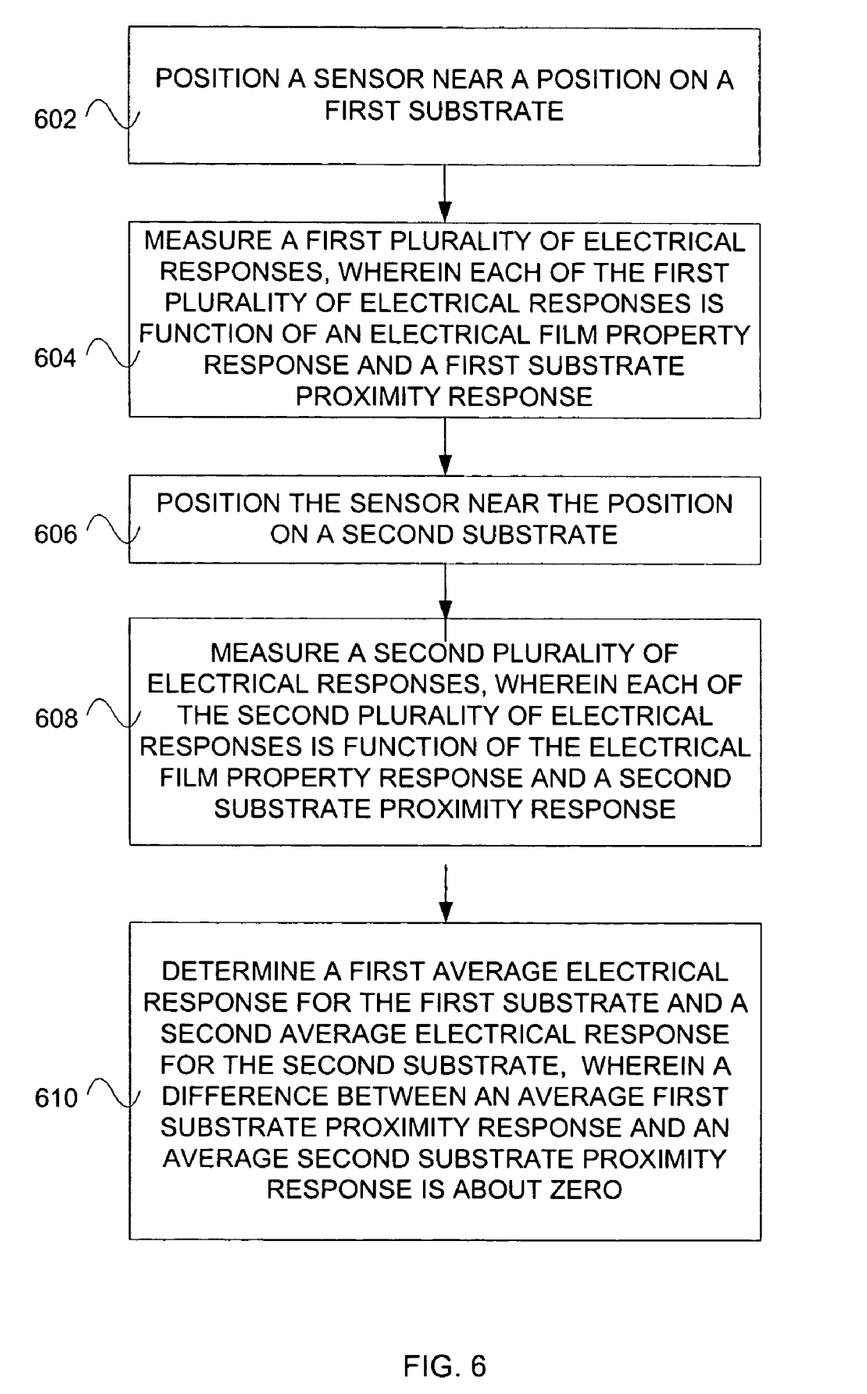
FIG. 6 illustrates a simplified diagram showing a method of determining an average electrical response to a conductive layer on a set of substrates vibrating about a vibration mean, according to one embodiment of the invention.

Referring now to FIG. 6, a simplified diagram showing a method of determining an average electrical response to a conductive layer on a set of substrates vibrating about a vibration mean, according to one embodiment of the invention. First, a first sensor is positioned near a position on a first substrate, at step 602. Next, a first plurality of electrical responses is measured, wherein each of the first plurality of electrical responses is function of an electrical film property response and a first substrate proximity response, at step 604. The sensor is positioned near the position on a second substrate, at step 606. Next, a second plurality of electrical responses is measured, wherein each of the second plurality of electrical responses is function of the electrical film property response and a second substrate proximity response, at step 608. Finally, a first average electrical response is determined for the first substrate and a second average electrical response for the second substrate, wherein a difference between an average first substrate proximity response and an average second substrate proximity response is about zero, at step 610.

While this invention has been described in terms of several preferred embodiments, there are alterations, permutations, and equivalents which fall within the scope of this invention. It should also be noted that there are many alternative ways of implementing the methods of the present invention. In addition, the invention is not limited to a particular sensor design, method of detection, excitation frequency, active or passive electrical components or any other peculiarities of a sensor vendor's method of reporting a sensible signal to be measured. Also, more than two sensors may be used.

Advantages of the invention include methods and apparatus for determining an average electrical response to a conductive layer on a substrate. Additional advantages include the use of less precise, and hence cheaper, substrate and sensor holders, the use of fewer and less precise sensors, the use of relatively inexpensive equipment to refine proximity correction, and higher substrate measurement throughput.

Having disclosed exemplary embodiments and the best mode, modifications and variations may be made to the disclosed embodiments while remaining within the subject and spirit of the invention as defined by the following claims.

What is claimed is:

1. A method of determining an average electrical response to a conductive layer on a set of substrates vibrating about a vibration mean, comprising:
   positioning a sensor near a position on a first substrate;
   measuring a first plurality of electrical responses, wherein each of said first plurality of electrical responses is function of an electrical film property response and a first substrate proximity response;
   positioning said sensor near said position on a second substrate;
   measuring a second plurality of electrical responses, wherein each of said second plurality of electrical responses is function of said electrical film property response and a second substrate proximity response; and
   determining a first average electrical response for said first substrate and a second average electrical response for said second substrate, wherein a difference between an average first substrate proximity response and an average second substrate proximity response is about zero.

2. Method of claim 1 wherein said vibration is randomized.

3. Method of claim 1 wherein said vibration is substantially periodic.

4. Method of claim 1 wherein each substrate rotates.

5. The method of claim 1, wherein said average electrical response for said first substrate and said second substrate is correlated to a thickness of said conductive layer.

6. The method of claim 1, wherein said average electrical response for said first substrate and said second substrate is correlated to a sheet resistance of said conductive layer.

7. The method of claim 1 correlating said average response to a metric of merit of said conductive layer.

8. The method of claim 1, wherein said measuring a plurality of first sensor electrical responses includes measuring voltages.

9. The method of claim 1, wherein said measuring a plurality of first sensor electrical responses, and said measuring a plurality of second sensor electrical responses, includes one of measuring voltages and measuring current.

10. A method of determining an average electrical response to a conductive layer on a substrate vibrating about a vibration mean, comprising:
    positioning a first sensor near a position on a first substrate;
    measuring a first plurality of electrical responses, wherein each of said first plurality of electrical responses is function of an electrical film property response and a first substrate proximity response;
    positioning a second sensor near said position on a said substrate;
    measuring a second plurality of electrical responses, wherein each of said second plurality of electrical responses is function of said electrical film property response and a second substrate proximity response, and wherein a mean value of said first substrate proximity response and said second substrate proximity response is about zero; and
    determining an average response of said plurality of said first plurality of electrical responses and said second plurality of electrical responses.

11. Method of claim 10 wherein said vibration is randomized.

12. Method of claim 10 wherein said vibration is substantially periodic.

13. Method of claim 10 wherein each of said set of substrates rotates.

14. The method of claim 10, wherein said average electrical response for said first substrate and said second substrate is correlated to a thickness of said conductive layer.

15. The method of claim 10, wherein said average electrical response for said first substrate and said second substrate is correlated a sheet resistance of said conductive layer.

16. The method of claim 10, wherein said average electrical response for said first substrate and said second substrate is correlated a sheet resistance of said conductive layer.

17. The method of claim 10 correlating said average response to a metric of merit of said conductive layer.

18. The method of claim 10, wherein said first sensor is positioned above said substrate and said second sensor is positioned below said substrate.

19. An apparatus of determining an average electrical response to a conductive layer on a substrate vibrating about a vibration mean, comprising:
    means of positioning a first sensor near a position on a first substrate;
    means of measuring a first plurality of electrical responses, wherein each of said first plurality of electrical responses is function of an electrical film property response and a first substrate proximity response;
    means of positioning a second sensor near said position on a said substrate;
    means of measuring a second plurality of electrical responses, wherein each of said second plurality of electrical responses is function of said electrical film property response and a second substrate proximity response, and wherein a mean value of said first substrate proximity response and said second substrate proximity response is about zero; and means of determining an average response of said plurality of said first plurality of electrical responses and said second plurality of electrical responses.

20. The apparatus of claim 19, wherein said first sensor is positioned above said substrate and said second sensor is positioned below said substrate.

* * * * *